United States Patent [19]

Mosbach et al.

[11] Patent Number: 4,648,995

[45] Date of Patent: Mar. 10, 1987

[54] CHEMICAL SYNTHESIS

[75] Inventors: Erwin H. Mosbach; Charles K. McSherry; Syoji Kuroki, all of New York, N.Y.

[73] Assignee: Beth Israel Medical Center, New York, N.Y.

[21] Appl. No.: 751,552

[22] Filed: Jul. 3, 1985

Related U.S. Application Data

[63] Continuation-in-part of Ser. No. 548,078, Nov. 2, 1983, Pat. No. 4,545,938.

[51] Int. Cl.$^4$ ................................................ C07J 9/00
[52] U.S. Cl. .................................................. 260/397.1
[58] Field of Search ....................................... 260/397.1

[56] References Cited

U.S. PATENT DOCUMENTS 4,545,938 10/1985 Mosbach et al. ................ 260/397.1

OTHER PUBLICATIONS

Merck Index (1976) Ninth edition p. 2197.
Fieser et al (1959) "Steroids" Pub. Reinhold publishing Corp., pp. 440-443.

Primary Examiner—Elbert L. Roberts

[57] ABSTRACT

A compound of the formula,

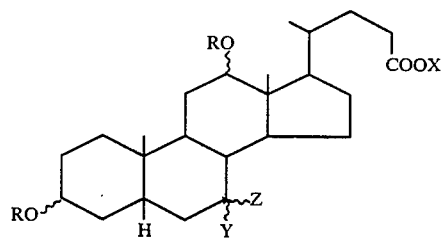

wherein R may be H or acyl; X may be H, acyl, or lower alkyl; Z may be H, hydroxy, or acyloxy; Y may be lower alkyl, aryl, alkyl substituted aryl or vinyl; and the non-toxic pharmaceutically acceptable salts thereof.

This invention was made in the course of work performed under a grant from the United States National Heart Lung and Blood Institute.

2 Claims, 8 Drawing Figures

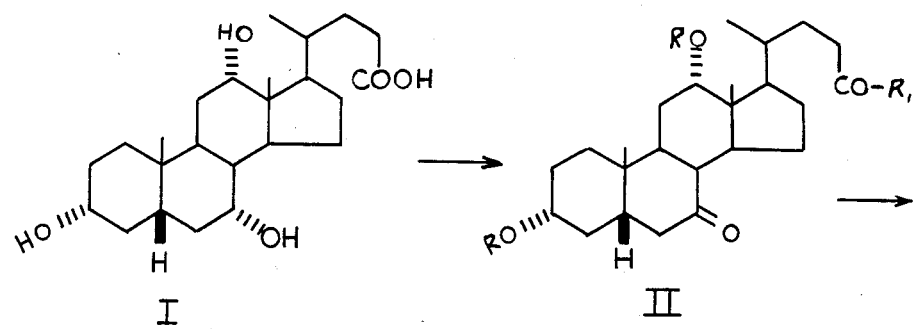
a. R=H; R₁=OH
b. R=CHO; R₁=OH
c. R=CHO; R₁=NHC(CH₃)₂CH₂OH
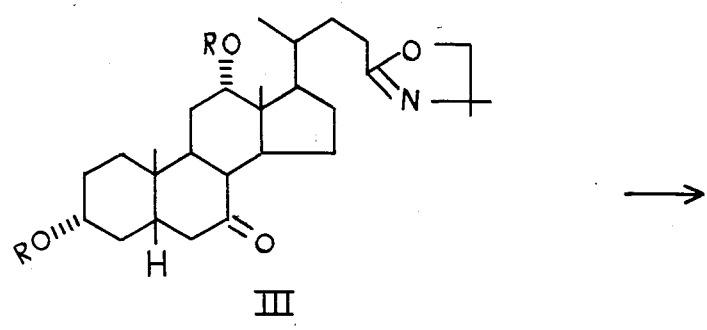
III
a. R=CHO
b. R=H
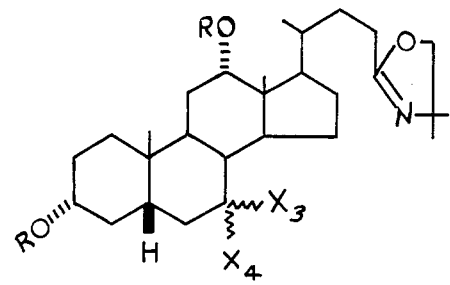
IV
a. X₃=αOH; X₄=βCH₃
b. X₃=βOH; X₄=αCH₃

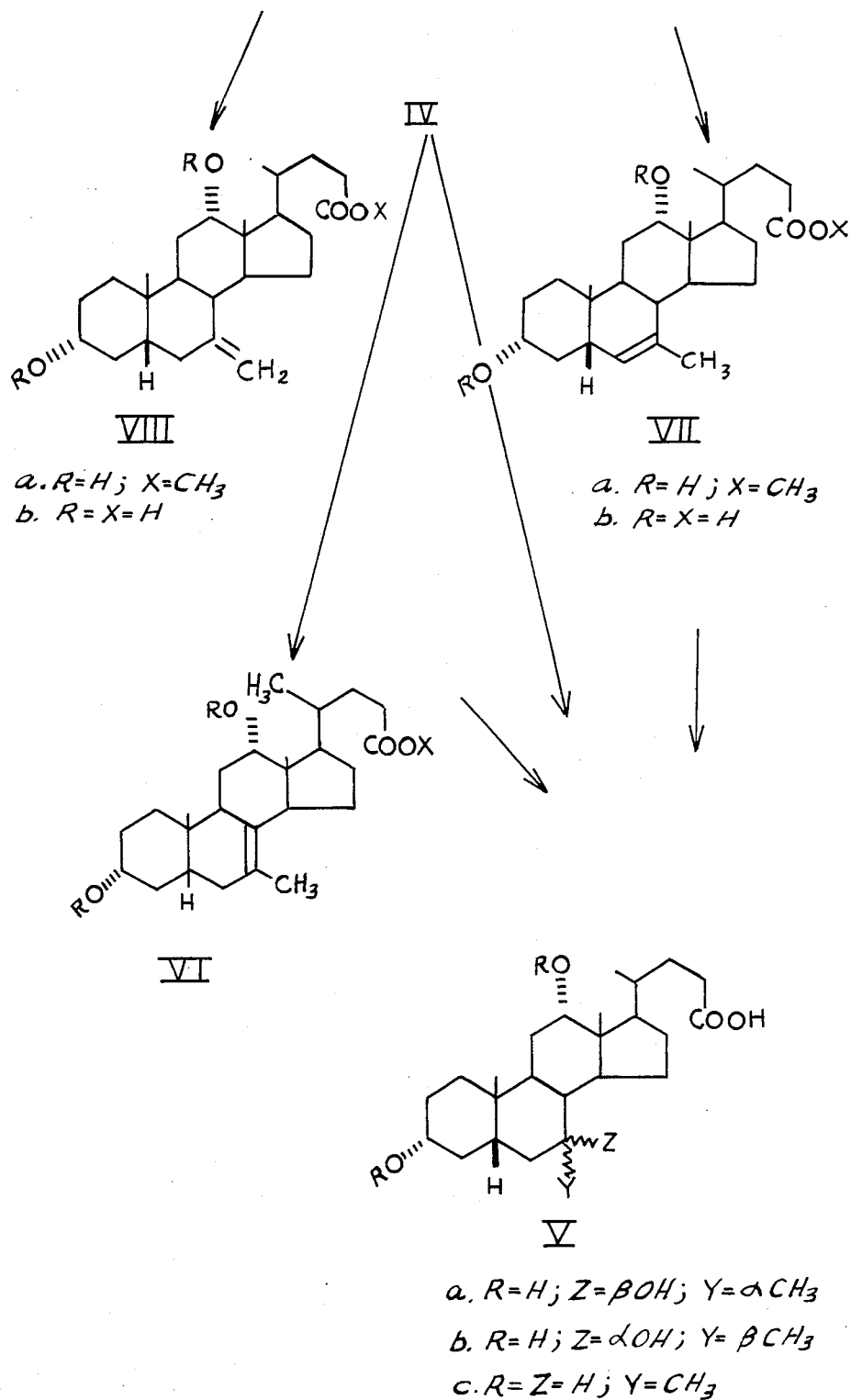

CHEMICAL SYNTHESIS

This application is a continuation-in-part application of previously filed, pending application Ser. No. 548,078, filed Nov. 2, 1983, now U.S. Pat. No. 4,545,938.

This invention relates to and has as its objective the provision of novel compounds and new processes for their production. More particularly, this invention relates to the production of new physiologically active steroidal compounds and to novel processes for their production.

The final physiologically active compounds of this invention are compounds of the formula,

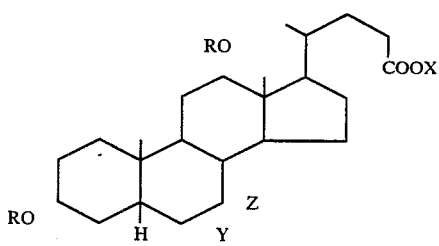

wherein R may be H or acyl; X may be H, acyl or lower alkyl; Z may be H, hydroxy or acyloxy; Y is lower alkyl; and the non-toxic, pharmaceutically acceptable salts thereof. In its most preferred embodiment, the practice of this invention provides compounds of the above formula, wherein R is H or acyl; X is H, acyl or methyl; Z is H, hydroxy or acyloxy; Y is methyl; and the non-toxic, pharmaceutically acceptable salts thereof, although the other final compounds of this invention also provide satisfactory results.

The final compounds of this invention are physiologically active compounds and may be employed in the therapeutic treatment of cholelithiasis disease in the same manner and to the same extent as disclosed for the 3,7-dihydroxy-cholanic acid derivatives in U.S. Pat. No. 3,859,437 issued Jan. 8, 1975, and as further described in Danziger, et al, Vol. 286, New England Journal of Medicine, pp 1–8 (1972) and Makino, et al, Vol. 72, Japan Journal of Gastroenterology, pp 690–702 (1975). The amounts and periods of administration of the compounds of the instant invention to the patient being treated therewith is within the purview of the knowledge of the skilled worker and will depend on the condition of the patient being treated and the result desired.

In order to obtain the satisfactory results from the instant invention is will be necessary to administer the compounds of the instant invention to the patient being treated by a systemic route, for example, perorally, or parenterally. The compositions employed for such purposes should contain the compounds of this invention in a suitable systemically administerable, pharmaceutically acceptable composition, all as is well known to the skilled worker. Thus, suitable injectable compositions, orally administerable pills, capsules or elixirs or other suitable, pharmaceutically acceptable compositions containing the active compounds of this invention may be employed in the practice thereof. The skilled worker is well equipped to determine the most suitable compositions and dosage forms to be employed in the practice of the instant invention.

The acyl moieties which may be employed in the practice of this invention include those acyl groups which are derived from hydrocarbon carboxylic acids of twelve carbon atoms or less and include such acids as the alkanoic, cycloalkanoic, monocyclic acyl and monocyclic aralkyl acids.

Whenever in the specification hereof and the claims appended thereto in any structural formula contained therein a curved line ( ) is employed in the linkage of atoms, it is meant to denote that the substituent moiety may be, stereochemically, in either the α- or β-position, depending upon the compound involved.

The final compounds of this invention may be prepared in accordance with the processes of this invention employing cholic acid as the starting material.

The process of the instant invention may be illustrated by the following equations:

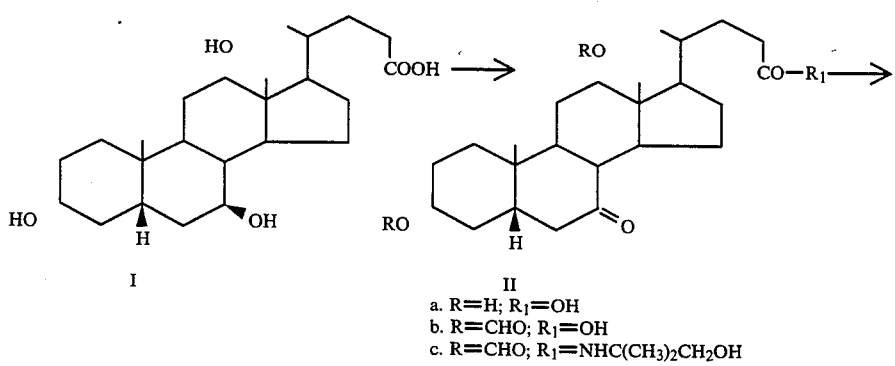

a. R=H; R$_1$=OH
b. R=CHO; R$_1$=OH
c. R=CHO; R$_1$=NHC(CH$_3$)$_2$CH$_2$OH

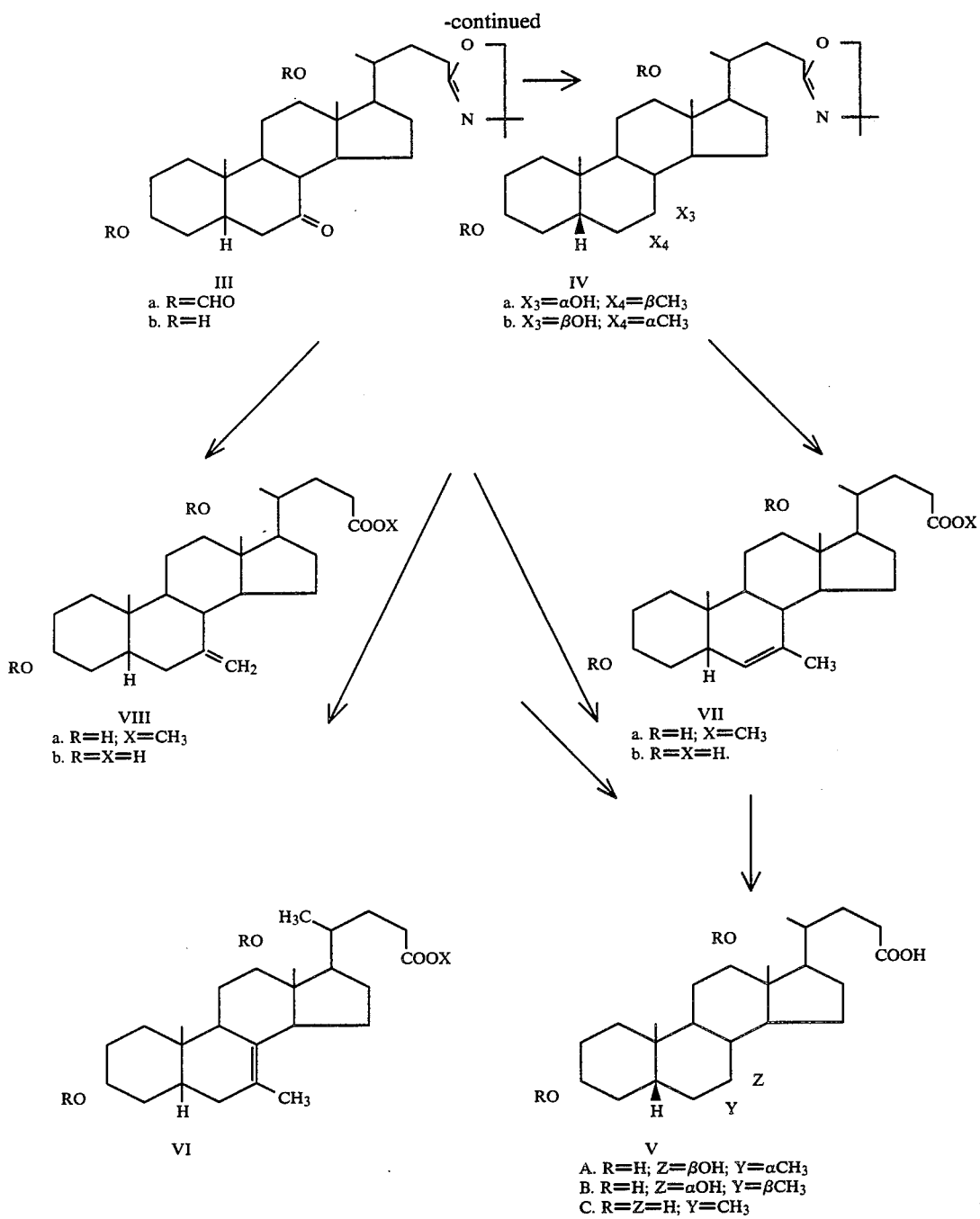

The cholic acid starting material (Compound I) is first oxidized to yield the corresponding 7-keto intermediate compounds (Compound II) which are then treated to yield the 7-keto-24-oxazoline derivatives (Compound III). The thus obtained oxazoline compounds (Compounds III) are then subjected to a Grignard reaction by treatment with a Grignard reagent of the formula RMgX, followed by acid hydrolysis to yield the 7-R-substituted cholanoic acids (Compounds V) as well as the 7-R-substituted cholenoic acid compounds (Compounds VI and VII), and the 7-alkylene-cholanoic acid compounds (Compounds VIII). The Grignard reagent, RMgX may be one wherein X is halogen and R selected from the group consisting of alkyl, aryl, alkyl substituted aryl, and vinyl. The 7-alkyl-cholenoic acid compounds (Compounds VII) and 7-alkylene cholanoic compounds (Compounds VIII) may then be hydrogenated to yield the 7-alkyl cholanoic acid compounds (Compounds IX).

The invention may be further illustrated by the following examples:

EXAMPLE 1

3α,12α-Diformyloxy-7-oxo-5β-cholan-24-oic acid

Cholic acid (80 g) was recrystallized twice from methanol and treated with N-bromosuccinimide as described by Fieser, et al., Vol. 71, Journal of the American Chemical Society pp 3935–3938 (1949). The resulting 3α,12α-dihydroxy-7-oxo-5β-cholan-24-oic acid (40 g) was dissolved in 100 ml of 97% formic acid and the solution was heated at 65° C. overnight. Evaporation of the solvent gave an oily residue, which was crystallized from aqueous ethanol. Recrystallizations from aqueous ethanol yielded 30 g of colorless needles of 3α,12α-diformyloxy-7-oxo-5β-cholan-24-oic acid, melting at 208°–211° C. PMR (δ ppm): 0.68 (3H, s, 18—CH$_3$), 0.93 (3H, d, J=6 Hz, 21—CH$_3$), 1.08 (3H, s, 19—CH$_3$), 4.73 (1H, m, 3β—H), 5.24 (1H, m, 12β—H), 8.03 and 8.18 (2H, s, 2×—COH).

EXAMPLE 2

2-(3α,12α-Diformyloxy-7-oxo-5β-cholan-24-amido)-2-methyl-1-propanol

To a stirred solution of 3α,12α-diformyloxy-7-oxo-5β-cholan-24-oic acid (19 g) in 400 ml of ethyl acetate were added 8.0 ml of triethylamine, a solution of 6.0 ml of 2-amino-2-methyl-1-propanol in 50 ml of ethyl acetate, and 15 g of N-ethoxycarbonyl-2-ethoxy-1,2-dihydroquinoline and the mixture was refluxed for 5 hrs. After cooling to room temperature, the reaction mixture was washed successively with water (50 ml×1), 1N HCl solution (50 ml×4), water (50 ml×1), 5% NaHCO$_3$ solution (50 ml×2), and then water to neutrality (50 ml×3). The organic layer was dried over anhydrous Na$_2$SO$_4$, filtered, and evaporated in vacuo to give an oily residue (21.5 g) which could not be crystallized. PMR (δ ppm): 0.66 (3H, s, 18—CH$_3$), 0.85 (3H, d, J=6 Hz, 21—CH$_3$), 1.08 (3H, s, 19—CH$_3$), 1.53 (6H, s, —C(CH$_3$)$_2$—), 3.88 (2H, s, —CH$_2$OH), 4.71 (1H, m, 3β—H), 5.22 (1H, m, 12β—H), 7.58 (1H, s, —NH—), 8.03 and 8.18 (2H, s, 2×—COH).

EXAMPLE 3

2-(3α,12α-dihydroxy-7-oxo-5β-cholan-24-amido)-2-methyl-1-propanol

The diformyl amide obtained in Example 2 (2 g) was hydrolyzed with 5% methanolic KOH (reflux, 1 hr). Dilution with water and extraction with ethyl acetate gave chromatographically pure 2-(3α,12α-dihydroxy-7-oxo-5β-cholan-24-amido)-2-methyl-1-propanol which was recrystallized from ethyl acetate (colorless prisms), melting at 229°–231° C. PMR (δ ppm): 0.70 (3H, s, 18—CH$_3$), 1.09 (3H, d, J=6 Hz, 21—CH$_3$), 1.16 (3H, s, 19—CH$_3$), 1.52 (6H, s, —C(CH$_3$)$_2$—), 3.65 (1H, m, 3β—H), 3.86 (2H, s, —CH$_2$OH), 4.09 (1H, m, 12β—H), 7.54 (1H, s, —NH—).

EXAMPLE 4

2-(3α,12α-Dihydroxy-7-oxo-24-nor-5β-cholanyl)-4,4-dimethyl-2-oxazoline 2-(3α,12α-Diformyloxy-7-oxo-5β-cholan-24-amido)-2-methyl-1-propanol obtained in Example 2, (11.2 g) was dissolved in 60 ml of tetrahydrofuran. Freshly distilled thionyl chloride (7.0 ml) was added dropwise to the stirred ice-cooled solution and the reaction mixture was stirred further for 1 hour. The solution was added slowly to 300 ml of stirred, ice-cooled diethyl ether and the white precipitate that formed was collected by filtration and quickly dissolved in a mixture of saturated NaHCO$_3$:diethyl ether (1:1, v/v). The ethereal extract was washed with water until netural, dried over anhydrous Na$_2$SO$_4$, and evaporated to dryness. The colorless oily residue was chromatographically pure 2-(3α,12α-diformyloxy-7-oxo-24-nor-5β-cholanyl)-4,4-dimethyl-2-oxazoline (10.4 g), which could not be crystallized. PMR (δ ppm): 0.67 (3H, s, 18—CH$_3$), 0.88 (3H, d, J=6 Hz, 21—CH$_3$), 1.08 (3H, s, 19—CH$_3$), 1.23 (6H, s, —C(CH$_3$)$_2$—), 3.80 (2H, s, —OCH$_2$—), 4.72 (1H, m, 3β-H), 5.23 (1H, m, 12β—H), 8.01 and 8.17 (2H, s, 2×—COH).

EXAMPLE 5

2-(3α,12α-dihydroxy-7-oxo-24-nor-5βcholanyl)-4,4-dimethyl-2-oxazoline

The diformyloxyoxazoline obtained in Example 4, (9.4 g) was hydrolyzed as described above and the resulting 2-(3α,12α-dihydroxy-7-oxo-24-nor-5β-cholanyl)-4,4-dimethyl-2-oxazoline (7.9 g) was crystallized from ethyl acetate. Repeated crystallizations from ethyl acetate yielded colorless prisms of pure oxazoline, melting at 174°–175° C. PMR (δ ppm): 0.73 (3H, s, 18—CH$_3$), 1.12 (3H, d, J=6 Hz, 21—CH$_3$), 1.16 (3H, s, 19—CH$_3$), 1.23 (6H, s, —C(CH$_3$)$_2$—), 3.65 (1H, m, 3β—H), 3.80 (2H, s, —OCH$_2$—), 4.10 (1H, m, 12β—H).

EXAMPLE 6

2-(3α,7ξ,12α-Trihydroxy-7ξ-methyl-24-nor-5β-cholanyl)-4,4-dimethyl-2-oxazoline

To a solution of 2-(3α,12α-dihydroxy-7-oxo-24-nor-5β-cholanyl)-4,4-dimethyl-2-oxazoline (5.0 g) dissolved in 200 ml of dry benzene was added dropwise with stirring a 3.0M ethereal solution of methyl magnesium iodide (20 ml) and benzene (20 ml). The reaction mixture was refluxed for 2 hours and then stirred at room temperature for 2 hours. A saturated NH$_4$Cl solution (200 ml) was added with vigorous stirring. The benzene layer was separated and the aqueous layer was then extracted twice with ethyl acetate. The organic extracts were combined, washed successively with water (50 ml×1), 10% Na$_2$S$_2$O$_3$ solution (50 ml×1), and water to neutrality (50 ml×3), dried over anhydrous Na$_2$SO$_4$, and evaporated to dryness. Repeated crystallizations from acetone and then from ethyl acetate of the residue (5.1 g) gave colorless prisms of 2-(3α,7ξ,12α-trihydroxy-7ξ-methyl-24-nor-5β-cholanyl)-4,4-dimethyl-2-oxazoline. Melting point, 103°–104.5° C. PMR (δ ppm): 0.80 (3H, s, 18—CH$_3$), 0.94 (3H, s, 19—CH$_3$), 1.18 (3H, d, J=6 Hz, 21—CH$_3$), 1.22 (6H, s, —C(CH$_3$)$_2$—), 1.37 (3H, s, 7ξ—CH$_3$), 3.66 (1H, m, 3β—H), 3.81 (2H, s, —OCH$_2$—), 4.10 (1H, m, 12β—H).

EXAMPLE 7

3α,7β,12α-Trihydroxy-7α-methyl-5β-cholan-24-oic acid and 3α,7α,12α-trihydroxy-7β-methyl-5β-cholan-24-oic acid 2-(3α,7ξ,12α-Trihydroxy-7ξ-methyl-24-nor-5β-cholanyl)-4,4-dimethyl-2-oxazoline, from Example 6, (2.8 g) was dissolved in 400 ml of 0.1N HCl solution and incubated at 37° C. for 3 days. The clear solution was decanted and the oily precipitate was dissolved in ethyl acetate (400 ml). The ethyl acetate solution was washed to neutrality, dried, and evaporated to dryness. The mixture of free acids (1.8 g), which showed three major spots on silica gel TLC, was treated with diazomethane and the resulting methyl ester derivatives were placed on a column of silica gel (150 g) and eluted with increasing concentrations of acetone in benzene. Fifteen percent acetone in benzene eluted a mixture of unsaturated dihydroxy compounds. The 7β-hydroxy isomer (320 mg) and the 7α-hydroxy isomer (400 mg) were eluted with 25% and 30% acetone in benzene, respectively. Alkaline hydrolysis of the two isomers with 5% methanolic KOH afforded the corresponding free acids, which were recrystallized from methanol-ethyl acetate: 3α,7β,12α-trihydroxy-7α-methyl-5β-cholan-24-oic acid, colorless prisms from methanol-ethyl acetate, mp 141°–142° C. PMR (δ ppm): 0.82 (3H, s, 18—CH$_3$), 1.01 (3H, s, 19—CH$_3$), 1.20 (3H, d, J=6 Hz, 21—CH$_3$), 1.46 (3H, s, 7α—CH$_3$), 3.66 (1H, m, 3β—H), 4.14 (1H, m, 12β—H); 3α,7α,12α-trihydroxy-7β-methyl-5β-cholan-24-oic acid, colorless prisms from methanol-ethyl acetate, mp 221°–223° C. PMR (δ ppm); 0.81 (3H, s, 18—CH$_3$), 0.94 (3H, s, 19—CH$_3$), 1.21 (3H, d, J=6 Hz, 21—CH$_3$), 1.37 (3H, s, 7β—CH$_3$), 3.64 (1H, m, 3β—H), 4.09 (1H, m, 12β—H).

EXAMPLE 8

3α,12α-Dihydroxy-7-methyl-5β-chol-7-en-24-oic acid; 3α,12α-dihydroxy-7-methyl-5β-chol-6-en-24-oic acid; and 3α,12α-dihydroxy-7-methylene-5β-cholan-24-oic acid 2-(3α,7ξ,12α-Trihydroxy-7ξ-methyl-24-nor-5β-cholanyl)-4,4-dimethyl-2-oxazoline from Example 6 (2.5 g) was dissolved in a solution of concentrated HCl (2 ml) and methanol (200 ml). The solution was refluxed for 6 hours, diluted with water, and extracted with ethyl acetate. The extract was washed with water, dried, and evaporated to dryness to give methyl ester derivatives of three hydration products. The residue was combined with the unsaturated dihydroxy fraction obtained in Example 7, (total, 2.6 g) and placed on a column of silica gel (150 g) impregnated with 15 g of AgNO$_3$. Elution with increasing proportions of acetone in chloroform yielded two major fractions. Fraction 1, eluted with 7% acetone in chloroform, gave 480 mg of an oily residue. Alkaline hydrolysis of the residue and recrystallizations from ethyl acetate yielded colorless prisms of 3α,12α-dihydroxy-7-methyl-5β-chol-7-en-24-oic acid. Melting point, 160°–163° C. PMR (δ ppm): 0.79 (3H, s, 18—CH$_3$), 0.86 (3H, s, 19—CH$_3$), 1.16 (3H, d, J=6 Hz, 21—CH$_3$), 1.73 (3H, s, 7—CH$_3$), 3.70 (1H, m, 3β—H), 4.13 (1H, m, 12β—H). Fraction 2, eluted with 10% acetone in chloroform, yielded, approximately, a 1:1 mixture of two unsaturated compounds (1.59 g) on AG-NO$_3$-TLC, GLC and GLC-MS. These two compounds were separated on a column of silica gel (150 g) impregnated with 15 g AgNO$_3$ using increasing concentrations of ethyl acetate in benzene. Elution with 35% ethyl acetate in benzene (Fraction 2A), followed by alkaline hydrolysis, afforded 640 mg of 3α,12α-dihydroxy-7-methyl-5β-chol-6-en-24-oic acid. Recrystallization from ethyl acetate gave colorless needles melting at 144°–148° C. PMR (δ ppm): 0.79 (3H, s, 18—CH$_3$), 0.89 (3H, s, 19—CH$_3$), 1.22 (3H, d, J=6 Hz, 21—CH$_3$), 1.69 (3H, s, 7—CH$_3$), 3.70 (1H, m, 3β—H), 4.13 (1H, m, 12β—H), 5.36 (1H, m, 6—H). Fraction 2B, eluted with 40% ethyl acetate in benzene, gave a second compound (450 mg) which, after alkaline hydrolysis, was recrystallized from ethyl acetate to give colorless needles of 3α,12α-dihydroxy-7-methylene-5β-cholan-24-oic acid, mp 199°–202° C. PMR (δ ppm): 0.79 (3H, s, 18—CH$_3$), 1.05 (3H, s, 19—CH$_3$), 1.20 (3H, d, J=6 Hz, 21—CH$_3$), 3.75 (1H, m, 3β—H), 4.16 (1H, m, 12β—H), 4.61 and 4.74 (2H, m, C=CH$_2$).

EXAMPLE 9

3α,12α-Dihydroxy-7ξ-methyl-5β-cholan-24-oic acid

The compounds obtained from Fractions 2A and 2B in Example 8 (320 mg) were dissolved in 50 ml of methanol and hydrogenated at 40 psi with 50 mg of PtO$_2$. The reaction mixture was filtered and the solvent was evaporated under reduced pressure. Crystallization from ethyl acetate yielded colorless needles of 3α,12α-dihydroxy-7ξ-methyl-5β-cholan-24-oic acid (210 mg). Melting point, 177°–179° C. PMR (δ ppm): 0.74 (3H, s, 18—CH$_3$), 0.95 (3H, s, 19—CH$_3$), 1.03 (3H, d, J=6 Hz, 7—CH$_3$), 1.17 (3H, d, J=6 Hz, 21—CH$_3$), 3.63 (1H, m, 3β—H), 4.11 (1H, m, 12β—H).

EXAMPLE 10

Following the procedure of Example 7, but substituting equivalent amounts of ethyl magnesium iodide or propyl magnesium iodide for the methyl magnesium iodide results in the preparation of the respective 7ξ-ethyl abnd 7ξ-propyl substituted analogs of the compounds obtained.

EXAMPLE 11

Following the procedure of Example 7, but substituting equivalent amounts of phenyl magnesium iodide, benzyl magnesium iodide, vinyl magnesium iodide, or cyclohexyl magnesium iodide for the methyl magnesium iodide results in the preparation of the respective 7-phenyl; 7-benzyl; 7-vinyl and 7-cyclohexyl substituted analogs of the compounds obtained, which may then be treated in accordance with the procedures of this invention to obtain the final products thereof.

EXAMPLE 12

It may be desirable to prepare the taurine and glycine conjugates of the free bile acid final products of this invention. These taurine and glycine conjugates may be prepared by the method described by Lack, et al. Vol. 14, *Journal of Lipid Research*, pages 367–370 (1973), which is as follows:

The free bile acid (1 mmole) dissolved in 95% ethanol is treated insolution with 1.4 mmole of N-ethoxy-carbonyl-2-ethoxy-1,2-dihydroxyquinoline dissolved in 95% ethanol. To this mixture there is added 1 mmole of taurine dissolved in dilute NaOH solution. The reaction mixture is then shaken for a period of 24 to 48 hours at 40° C. until all components form a homogeneous solution. The solution is diluted with water and extracted with ethyl acetate. The aqueous residue, containing the taurine-conjugated bile acid, is then evaporated to dryness. The residue is then crystallized from aqueous ethanol-ethyl acetate in the cold, filtered and the crystalline residue is washed with ether.

The invention may be otherwise included within the scope of the appended claims.

What is claimed is:

1. A compound of the formulae,

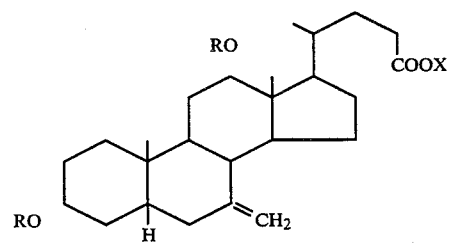

-continued
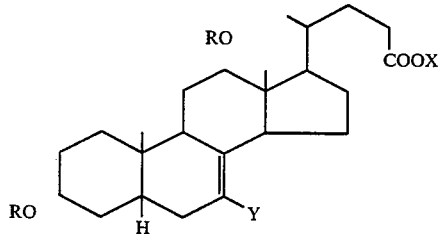
-continued
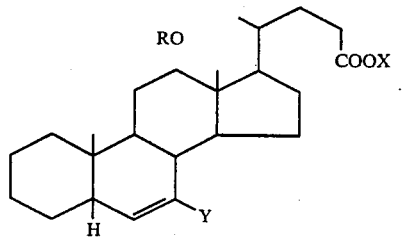
wherein R, is H or acyl; X is H, acyl or alkyl and Y is lower alkyl, aryl, alkyl substituted aryl, vinyl or cycloalkyl.
2. A compound of claim 1 wherein X is H; R is H; and Y is $CH_3$.
* * * * *